(12) United States Patent
    Patel et al.

(10) Patent No.: US 9,877,754 B2
(45) Date of Patent: Jan. 30, 2018

(54) MEDIAL-PLANTAR PLATE FOR MEDIAL COLUMN ARTHRODESIS

(71) Applicant: Wright Medical Technology, Inc., Memphis, TN (US)

(72) Inventors: Vinay Patel, Bartlett, TN (US); Mary McCombs-Stearns, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 320 days.

(21) Appl. No.: 14/420,240

(22) PCT Filed: Sep. 11, 2014

(86) PCT No.: PCT/US2014/055141
§ 371 (c)(1),
(2) Date: Feb. 6, 2015

(87) PCT Pub. No.: WO2016/039753
PCT Pub. Date: Mar. 17, 2016

(65) Prior Publication Data
US 2016/0256204 A1 Sep. 8, 2016

(51) Int. Cl.
*A61B 17/88* (2006.01)
*A61B 17/80* (2006.01)

(52) U.S. Cl.
CPC ...... *A61B 17/8014* (2013.01); *A61B 17/8057* (2013.01); *A61B 17/8061* (2013.01); *A61B 17/8052* (2013.01)

(58) Field of Classification Search
None
See application file for complete search history.

(56) References Cited

U.S. PATENT DOCUMENTS

2010/0121325 A1\* 5/2010 Tyber ................. A61B 17/1717
606/62
2010/0125300 A1 5/2010 Blitz et al.
(Continued)

FOREIGN PATENT DOCUMENTS

CN 103393458 A 11/2013
DK 1897509 T3 8/2009
(Continued)

OTHER PUBLICATIONS

Arthrex—Arthrex Releases Medial Column Fusion Plate [retrieved from internet on Aug. 24, 2016] <URL: https://www.arthrex.com/newsroom/product-updates/2014/07/01/arthrex-releases-medial-columnfusion-plate> publication date: undetermined.
(Continued)

*Primary Examiner* — Sameh Boles
(74) *Attorney, Agent, or Firm* — Duane Morris LLP

(57) ABSTRACT

An article comprises a unitary plate configured to conform to a foot of a patient. The plate has a dorsal portion shaped to conform to a dorsal surface of a medial column of the foot and a plantar-medial portion shaped to conform to a medial surface of a first metatarsal of the foot and extend to a plantar surface of the first metatarsal. The plantar-medial portion is integrally attached to the dorsal portion. The plate has a plurality of apertures for receiving screws. The apertures include: a plurality of first apertures through the dorsal portion, adapted to receive a respective one or more first screws to be inserted into a dorsal surface of a talus of the foot, and at least one second aperture adapted to receive a second screw inserted through a plantar end of the plantar-medial portion into a first metatarsal of the foot.

10 Claims, 12 Drawing Sheets

(56) References Cited

U.S. PATENT DOCUMENTS

| | | | |
|---|---|---|---|
| 2010/0217327 A1 | 8/2010 | Vancelette et al. | |
| 2010/0217328 A1 | 8/2010 | Terrill et al. | |
| 2010/0256687 A1 | 10/2010 | Neufeld et al. | |
| 2011/0093018 A1 | 4/2011 | Prasad et al. | |
| 2011/0245830 A1 | 10/2011 | Zgonis et al. | |
| 2013/0018424 A1 | 1/2013 | Subik | |
| 2013/0150899 A1 | 6/2013 | Sixto et al. | |
| 2013/0172942 A1* | 7/2013 | Lewis | A61B 17/8061 606/281 |
| 2014/0012328 A1 | 1/2014 | Prasad et al. | |

FOREIGN PATENT DOCUMENTS

| | | |
|---|---|---|
| JP | 2012-518467 A | 8/2012 |
| WO | 2010/098909 A1 | 9/2010 |
| WO | 2011/116377 A1 | 9/2011 |
| WO | 2015/195399 A1 | 12/2015 |

OTHER PUBLICATIONS

Patent Examination Report No. 1 issued in connection with Australian patent application No. 2014321174, dated Aug. 26, 2016, 7 pages.

International Searching Authority, Korean Intellectual Property Office, (PCT International Search Report regarding corresponding PCT Application No. PCT/US2014/055141 dated Jun. 4, 2015, pp. 1-7.

International Searching Authority, Korean Intellectual Property Office, PCT Written Opinion of the International Searching Authority regarding corresponding PCT Application No. PCT/US2014/055141 dated Jun. 4, 2015, pp. 1-7.

Japanese Office Action issued for corresponding Japanese patent application No. 2016-536160, dated Jun. 20, 2017, 6 pages.

First Office Action issued for corresponding Chinese patent application No. 201480006101.8, dated Aug. 14, 2017, 6 pages.

* cited by examiner

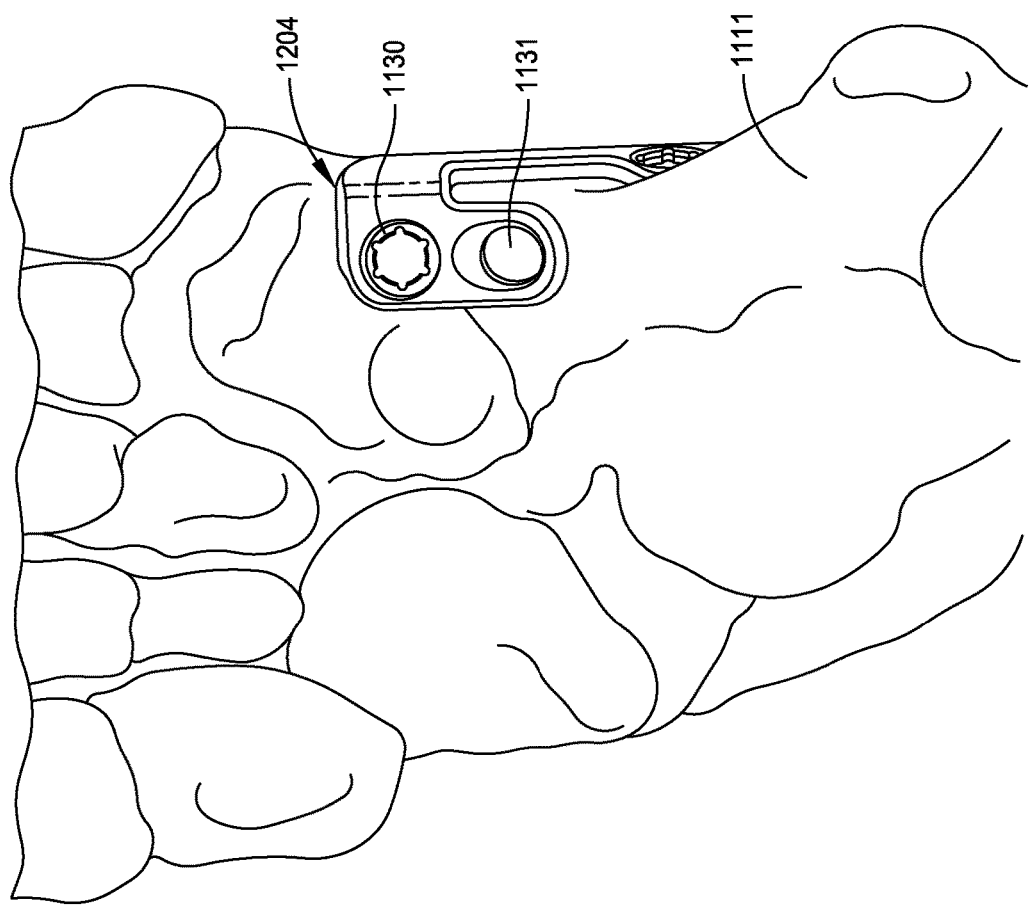

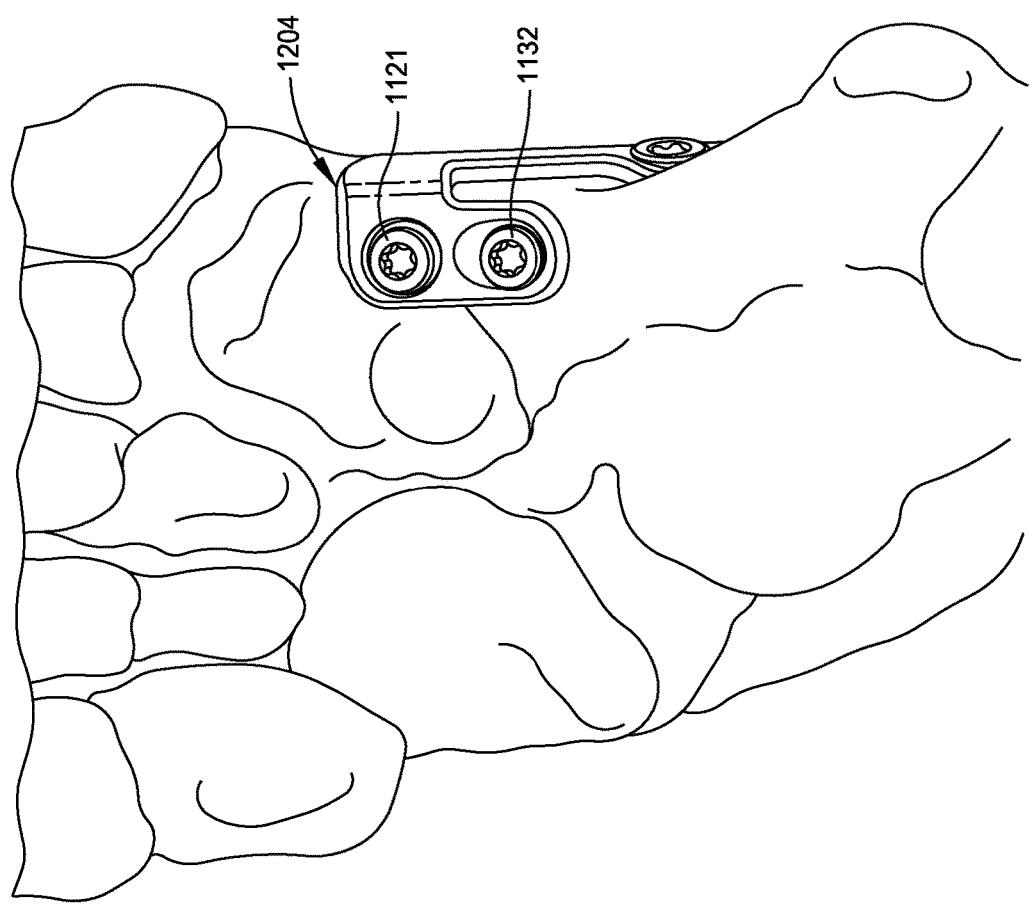

MEDIAL-PLANTAR PLATE FOR MEDIAL COLUMN ARTHRODESIS

FIELD

This application pertains generally to medical devices, and more particularly to an implant plate for use in medial column arthrodesis procedures, such as fusing damaged, deteriorating, or fractured talus, navicular, cuneiform and/or metatarsal bones.

BACKGROUND

Arthrodesis is a surgical procedure for artificially inducing joint ossification between two bones. Arthrodesis may be performed to relieve pain in a joint which cannot be managed by more conservative approaches, such as medication, splints, or the like. The typical causes of such pain are fractures which disrupt the joint, and arthritis. Arthrodesis may be performed for fusing damaged, deteriorating, or fractured tibia, talus and calcaneus bones in the ankle region. Arthrodesis may be used to treat Charcot midfoot deformity, including bone resection and/or osteotomy to reduce deformity.

Arthrodesis procedures often include fastening a bone plate to the surface of a bone, typically at both sides of a joint line to support and/or stabilize the joint. Bone plates have often been attached to the bones with bone screws that extend from the plate into the bone. In some examples, the head of the bone screw is locked to the plate (e.g., by threaded engagement between the screw head and the bone plate) and in other plates the head of the screw is free to angulate with respect to the plate, such that a polyaxial screw may be placed in the bone at a surgeon-selected angle. In yet other examples, the screw head may cooperate with the bone plate to provide compression or distraction of the joint (i.e., to push the bone fragments towards or away from one another).

Bone plates stabilize the treated bones to prevent relative motion between the bones during the prolonged fusion period, which may last for several months. Patients are typically advised to keep weight off of the treated foot during the fusion period. If, however, the patient is non-compliant and walks on the treated foot, the foot and bone plate are subjected to undesirable bending forces.

Improved bone plates are desired.

SUMMARY

In some embodiments, an article comprises a unitary plate configured to conform to a foot of a patient. The unitary plate has a dorsal portion shaped to conform to a dorsal surface of a medial column of the foot and a plantar-medial portion shaped to conform to a medial surface of a first metatarsal of the foot and extend to a plantar surface of the first metatarsal. The plantar-medial portion is integrally attached to the dorsal portion. The unitary plate has a plurality of apertures for receiving screws. The apertures include: a plurality of first apertures through the dorsal portion, including one or more apertures adapted to receive a respective one or more first screws to be inserted into a dorsal surface of a talus of the foot, and at least one second aperture adapted to receive a second screw inserted through a plantar end of the plantar-medial portion into a first metatarsal of the foot.

A method comprises: fastening a unitary plate to a foot of a patient, the unitary plate having a dorsal portion that conforms to a dorsal surface of a medial column of the foot and a plantar-medial portion that conforms to a medial surface of a first metatarsal of the foot and extends to a plantar surface of the first metatarsal, the plantar-medial portion integrally attached to the dorsal portion, the fastening including: inserting one or more screws through the dorsal portion into a talus of the foot, and inserting at least one additional screw through a plantar end of the plantar-medial portion into a first metatarsal of the foot.

BRIEF DESCRIPTION OF THE DRAWINGS

These and other features and advantages of the present disclosure are more fully disclosed in, or rendered obvious by, the following detailed description, which is to be considered together with the accompanying drawings wherein like numbers refer to like parts and further wherein:

FIG. 10A is a plantar view of the foot and plate of FIG. 9A.

FIG. 10B shows the foot and plate of FIG. 10A with screws inserted therein.

DETAILED DESCRIPTION

Figure 1:
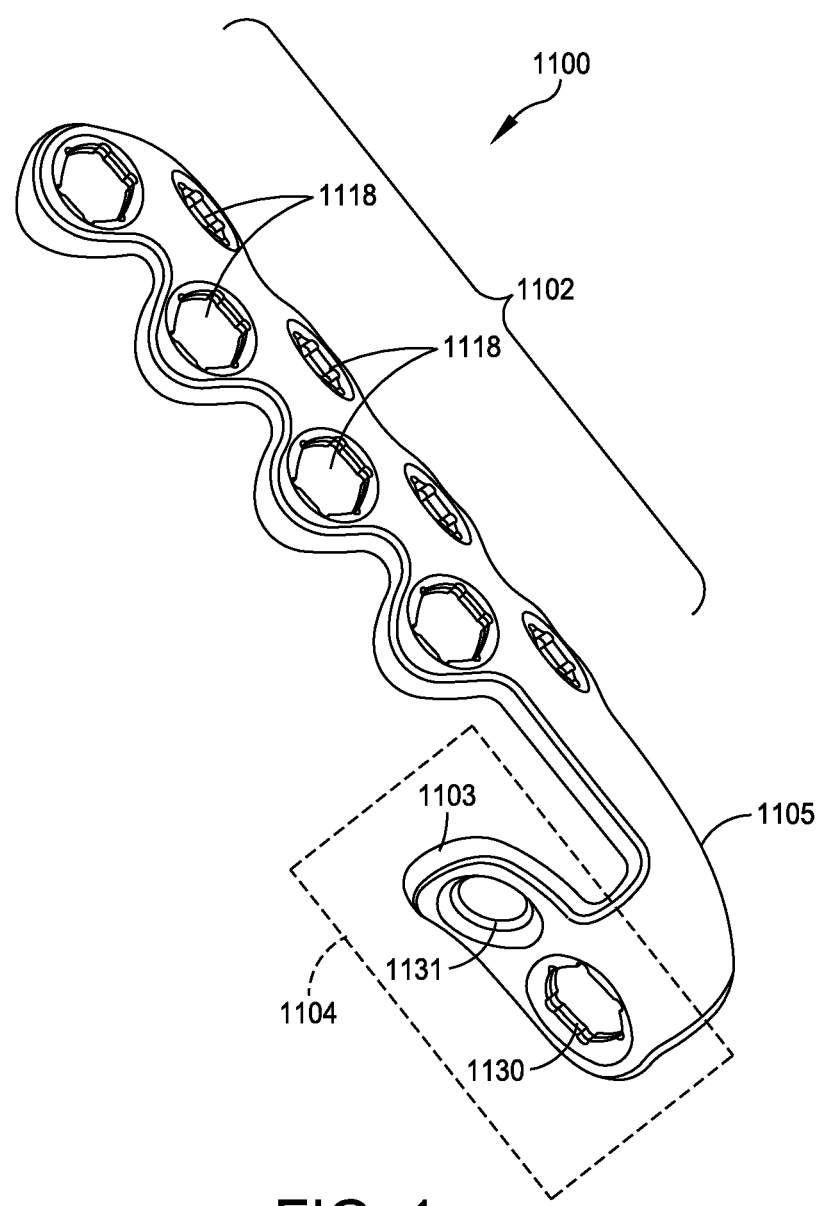
FIG. 1 is an isometric view of a medial-plantar medial tension bone plate according to an exemplary embodiment.
Figure 2:
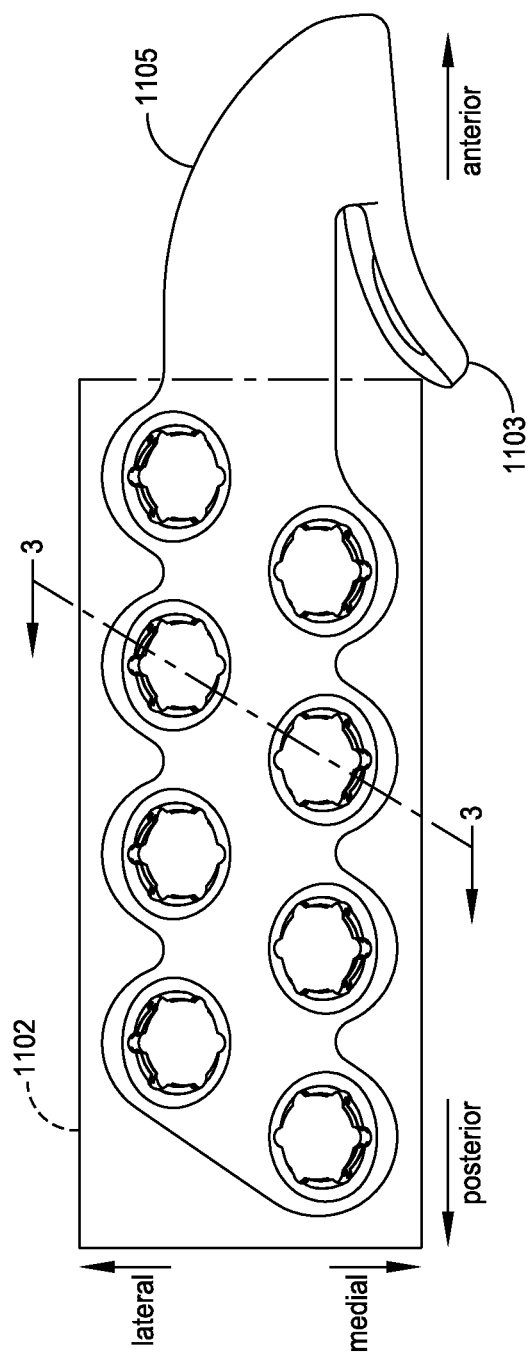
FIG. 2 is a top (dorsal) plan view of the bone plate of FIG. 1.
Figure 3:
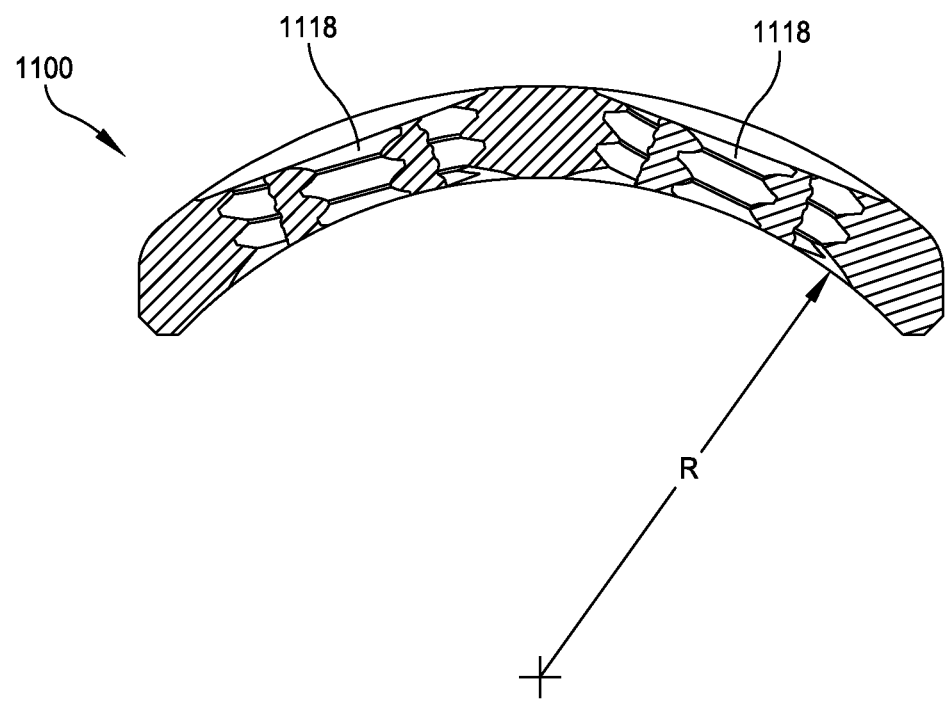
FIG. 3 is a cross-sectional view of the bone plate, taken along section line 3-3 of FIG. 2.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

FIGS. 1-4 show an exemplary embodiment of a medial-plantar medial-tension band plate 1100 for medial column arthrodesis. The bone plate 1100 can be used for medial column fusion or treatment of fractures, arthritis or Charcot foot.

Figure 4:
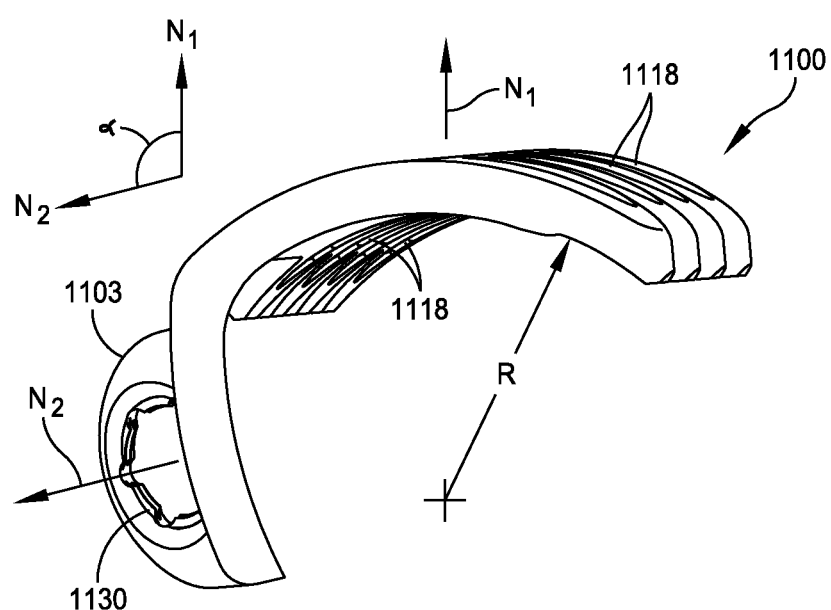
FIG. 4 is an anterior end elevation view of the bone plate of FIG. 1.
Figure 5:
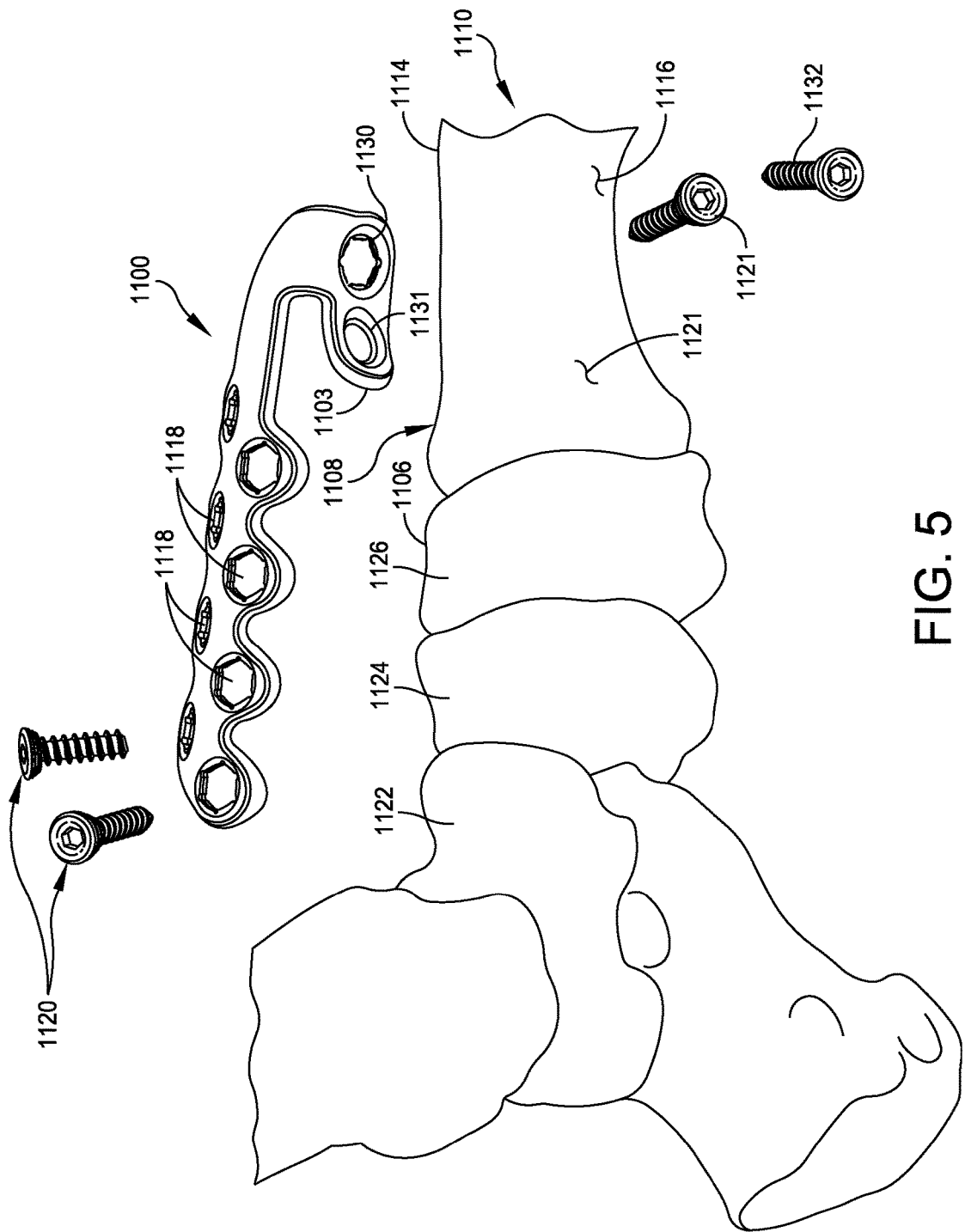
FIG. 5 is an exploded medial view of the bone plate of FIG. 1, with screws for attachment to the medial column of a patient's foot.
Figure 8:
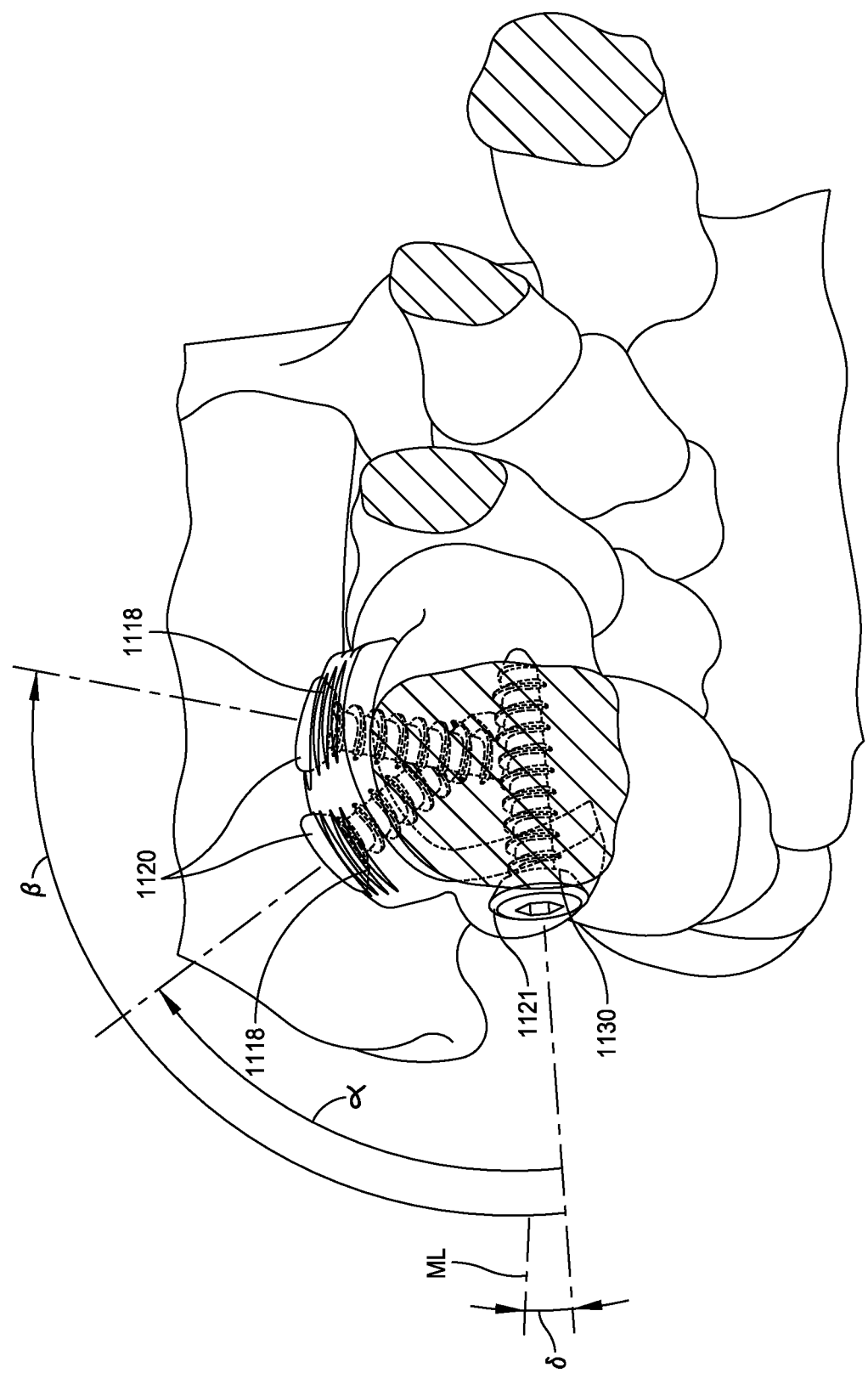
FIG. 8 is an anterior view of the foot with the plate implanted as shown in FIG. 7.
Figure 9A:
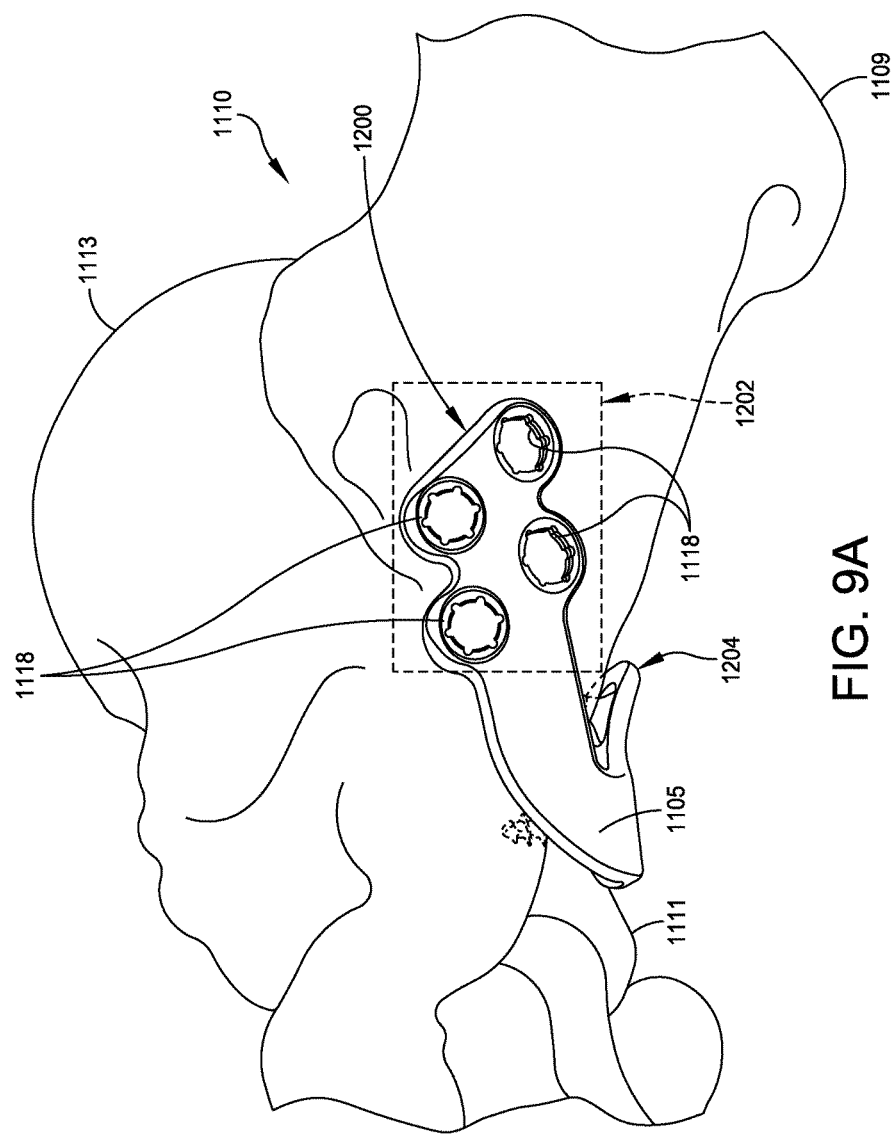
FIG. 9A is a lateral view of the foot with a plate according to a second embodiment.
Figure 9B:
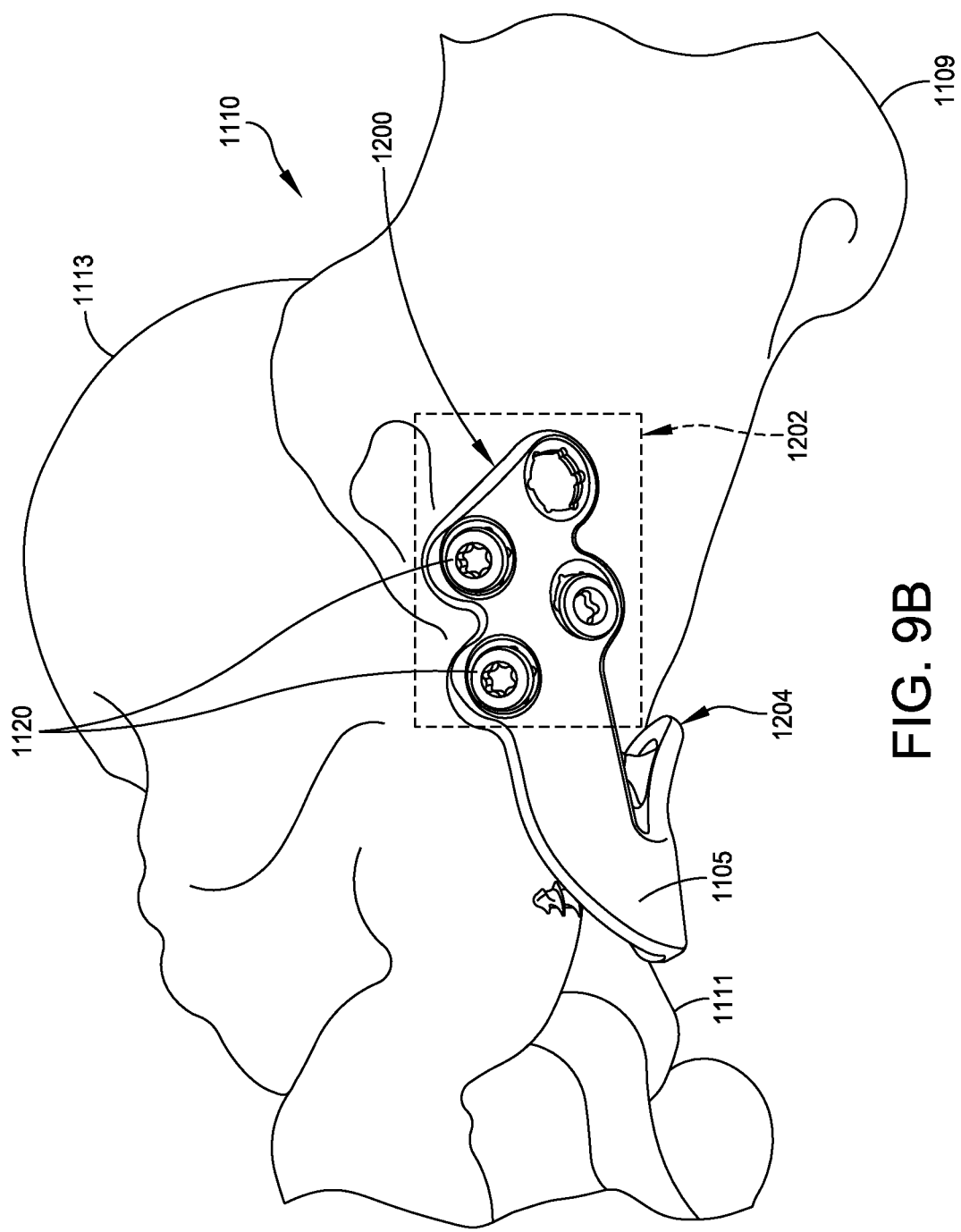
FIG. 9B shows the foot and plate of FIG. 9A with screws inserted therein.

The plate is a unitary plate 1100 configured to conform to a foot 1110 of a patient. The unitary plate 1100 has a dorsal portion 1102 shaped to conform to a dorsal surface 1106 of a medial column 1108 (FIG. 5) of the foot 1110, and a plantar-medial portion 1104 shaped to conform to a medial surface 1112 of a first metatarsal 1114 of the foot 1110. The plantar-medial portion 1104 is integrally attached to the dorsal portion 1102 by the connecting portion 1105. The plantar-medial portion 1104 is shaped to extend to a plantar surface 1116 of the first metatarsal 1114. As shown in FIGS. 4 and 8, the plantar-medial portion 1104 wraps around the medial surface of the first metatarsal 1114 in the plantar direction, creating a tension band with bone screws 1120 extending in approximately orthogonal directions.

The unitary plate 1100 has a plurality of apertures 1118, 1130 for receiving bone screws 1120. The apertures include first apertures 1118 and one or more second apertures 1130. The bone screws 1120 can be locking or non-locking bone screws.

The dorsal portion 1102 of the plate 1100 has a plurality of first apertures 1118 therethrough, including one or more apertures adapted to receive a respective one or more first bone screws 1120 to be inserted into a dorsal surface 1106 of a talus 1122 of the foot 1110. In some embodiments, the dorsal portion 1102 of the plate has a first (medial) row of first apertures 1118 and a second (lateral) row of first apertures 1118. The first row and second row of first apertures 1118 are configured to receive bone screws, which can be locking screws 1120 or non-locking screws. The second row of first apertures 1118 is longitudinally offset from the first row of first apertures 1118, to provide several insertion locations for bone screws. For optimal stability, at least one bone screw is inserted through the first apertures 1118 into each of the talus 1122, the navicular 1124, and the cuneiform 1126.

In some embodiments, the dorsal portion 1102 of the plate has a radius R on its bottom surface (FIGS. 3 and 4), which is substantially constant from the posterior end of the plate 1100 to the anterior-most aperture 1118 of the dorsal portion 1102. The radius can be the same for various bone plate sizes having different posterior-anterior lengths. For example, in some embodiments, the radius size is 0.53 inch. This radius size conforms comfortably to the dorsal surface of the bones 1122, 1124, 1126. In various embodiments, the posterior-anterior length and number of holes in the dorsal portion 1102 can be varied.

In some embodiments, the bone screws 1120 are 4 mm or 5.5 mm polyaxial screws, which can be inserted at any angle with a cone subtending about 15 degrees (e.g., from 13 to 17) from the center axis of the hole 1118. Polyaxial screws can be pointed in the direction towards the most dense bone, for better fixation. In some embodiments, the bone screws 1120 are oteopenic screws with a larger thread pitch, and a larger thread height between the major and minor diameters of the thread, which are favorable for patients with soft or deteriorated bones, such as Charcot patients.

The plantar-medial portion 1104 of the bone plate 1100 has at least one second aperture 1130 adapted to receive a second bone screw 1121 inserted through a plantar end of the plantar-medial portion 1104 into a first metatarsal 1114 of the foot 1110.

In some embodiments, the plantar-medial portion 1104 further includes a compression slot 1131. The compression slot 1131 is proximate an anterior end of the unitary plate 1100, distal from the first apertures 1118. In some embodiments, as shown in FIGS. 1 and 5-7, the plantar-medial portion 1104 has both a compression slot 1131 and at least one second aperture 1130. The compression slot 1131 is placed closest to the anterior end of the plantar-medial portion 1104 of the plate 1100. The compression slot 1131 has a ramped edge. The compression slot 1131 is configured to receive a non-locking screw 1132 which can be driven through the compression slot 1131 into the bone.

In some embodiments, the plantar-medial portion 1104 comprises an oblique portion extending in a posterior-medial direction, the oblique portion configured to conform to the first metatarsal 1114 of the foot 1110, and the second aperture 1130 is located in the oblique portion.

In some embodiments, the dorsal portion 1102 has a first average normal direction $N_1$ and the plantar-medial portion 1104 has a second average normal direction $N_2$, and an angle $\gamma$ between the first average normal direction $N_1$ and the second average normal direction $N_2$ is about 95 degrees or more.

In some embodiments, as best seen in FIG. 8, the first apertures 1118 and second apertures 1130 are oriented relative to each other so that an angle $\alpha$, $\beta$ between one of the first bone screws 1120 and the second bone screw 1121 after insertion is in a range from about 60 degrees to about 120 degrees. In some embodiments, a respective angle $\alpha$, $\beta$ between the compression screw and each of the one or more bone screws is in a range from about 75 degrees to about 90 degrees.

In some embodiments, the plate 1100 comprises a titanium alloy with a type-2 surface anodization to improve the titanium fatigue properties. In some embodiments, the alloy composition is defined by the ASTM F136-13 Standard Specification for Wrought Titanium-6Aluminum-4Vanadium ELI (Extra Low Interstitial) Alloy for Surgical Implant Applications (UNS R56401). In some embodiments, the plate has a thickness of 2.5 mm. In other embodiments, the plate can be thicker, or the plate 1100 can comprise stainless steel.

In some embodiments, the unitary plate 1100 is fastened to the foot 1110 as part of a medial column 1108 fusion for treating neuropathic osteoarthropathy. In some embodiments, the plate 1100 is used for a Charcot procedure. The plate 1100 can be inserted while the patient's foot is immobilized in a circular fixator or other external fixation device for the duration of fusion.

In some embodiments, for performing fusion the surgeon first trims the joints of the medial column of the foot to remove cartilage.

The fixation method then comprises fastening a unitary plate 1100 to a foot 1110 of a patient. The unitary plate 1100 has a dorsal portion 1102 that conforms to a dorsal surface 1106 of a medial column 1108 of the foot 1110 and a plantar-medial portion 1104 that conforms to a medial surface 1112 of a first metatarsal 1114 of the foot 1110 and extends to a plantar surface 1116 of the first metatarsal 1114. The plantar-medial portion 1104 is integrally attached to the dorsal portion 1102. In some embodiments, the fastening includes inserting one or more bone screws 1120 through the dorsal portion 1102 into the talus 1122 of the foot 1110.

In preparation, the surgeon threads a drill guide (not shown) into the apertures 1118 that are to receive bone screws 1120, and drills through the guide to the appropriate depth.

In some embodiments, one or two of the first bone screws 1120 are first inserted through the most posterior holes 1118 into the talus 1122.

In some embodiments, a compression screw 1132 is then inserted through a compression slot 1131 in the plantar-medial portion 1104. In some embodiments, the step of inserting the compression screw 1132 causes compression of the medial column 1108, to compress all joints until the bones of the medial column start touching each other. The compression slot 1131 has a ramped edge. A non-locking screw 1132 is positioned at the most anterior (distal) end of the compression slot 1131 and driven through the compression slot 1131 into the bone. As the head of the non-locking screw 1132 is driven into the compression slot 1131, the head rides along the anterior ramp of the compression slot and centers itself in the aperture 1131, applying a force on the plate 1100 to pull the posterior end of the plate (and the talus 1122) in the anterior direction. The amount of tension can be determined by the geometry of the compression slot and its ramp. For example, in some embodiments, the compression slot causes 5 mm of compression. That is, the bone screws 1120 inserted through the dorsal portion 1102 of the plate 1100 are drawn 5 mm closer to the anterior end of the first metatarsal 1114.

After inserting the compression screw 1132, at least one additional bone screw 1121 is inserted through the aperture 1130 in the plantar end of the plantar-medial portion 1104, till the bone screw is inserted into a first metatarsal 1114 of the foot 1110. The bone screw 1121 can be a locking screw or a non-locking screw. In some embodiments, the bone screw 1121 is a polyaxial screw. In some embodiments, the bone screw is an osteopenic screw. In some embodiments, the bone screw 1121 is inserted from an angle $\delta$ of 15 to 20 degrees below the medial-lateral axis ML, so that the insertion angle of bone screw 1121 has a dorsal component of about 15 to about 20 degrees.

The surgeon inserts additional bone screws 1120 into the dorsal portion 1102 of the plate. In some embodiments, the surgeon inserts a bone screw 1120 into each of the remaining holes 1118 which overlies bone (and does not overlie a joint). In embodiments in which the dorsal portion 1102 of the plate has a first row of holes and a longitudinally offset second row of holes, the surgeon can insert one or more locking bone screws 1120 through the first and second rows of holes, into one or more of the talus 1122, navicular 1124 or cuneiform 1126 bones. The screws 1120 are placed within a 30 degree purchase-cone so that bone screws 1120 always purchase the bones of talus 1122, navicular 1124 and cuneiform 1126, i.e., always acquire a leveraged and secure engagement between the threads on the surface of bone screw 1120 and the interior of the bone as the screw is rotated inwardly toward the bone.

In some embodiments, the step of inserting the one or more bone screws includes inserting at least one bone screw 1120 in each of the talus 1122, the navicular 1124, and the cuneiform 1126. In some embodiments, the step of inserting the one or more bone screws includes inserting at least two bone screws 1120 in each of the talus 1122, the navicular 1124, and the cuneiform 1126. In some embodiments, two bone screws are inserted into each bone 1122, 1124, 1126, including one bone screw in the first longitudinal row, and one bone screw in the second longitudinal row.

In some embodiments, in which the plantar-medial portion 1104 comprises an oblique portion 1103 extending in a posterior-medial direction, the oblique portion 1103 conforms to the first metatarsal 1114, and the at least one additional bone screw 1121 is a locking bone screw 1120 inserted into the oblique portion 1103.

In some embodiments, a respective angle $\alpha$, $\beta$ between the compression screw and each of the one or more bone screws is in a range from about 60 degrees and about 120 degrees.

In some embodiments, the dorsal portion 1102 has a first average normal direction $N_1$ and the plantar-medial portion 1104 has a second average normal direction $N_2$, and the bone screws 1120 inserted through the holes 1118 in the dorsal portion 1102 are separated from the bone screw(s) 1121 inserted into the plantar-medial portion 1104 by an angle $\gamma$ of about 90 to about 95 degrees. In some embodiments, the angle $\gamma$ is about 95 degrees (e.g., 93 or 97 degrees).

The plates described herein can be applied for either medial column or lateral column arthrodesis. The same plate 1100 can be used in the position shown in FIGS. 1-8 for medial column arthrodesis, with the dorsal portion 1102 of the plate on the dorsal side of the foot. Alternatively, the plate can be rotated approximately 180 degrees (about its anterior-posterior axis) and used for lateral column arthrodesis. When used for lateral column arthrodesis, the portion 1102 is applied to the lateral side of the foot, and the portion 1104 is applied to the plantar-lateral side of the foot.

The plates described herein can also be varied in length. In some embodiments, the same length plate 1100 can be used for medial column and lateral column fixation. In other embodiments plates of different length can be used for medial column and lateral column fixation. A surgeon can select the length of the plate based on the size and density of the patient's bones. In some embodiments, the same size and shape of portion 1104 can be used while varying the length of the portion 1102.

FIGS. 9A to 11 show a second embodiment of the plate 1200, which is shorter in length than the plate 1100. FIGS. 9A-11 show the use of the plate 1200 for lateral column arthrodesis. As discussed above, the same plate 1200 could also be used for medial column arthrodesis, by rotating the plate 180 degrees about the anterior posterior axis. As shown in FIGS. 9A-11, in some embodiments, the plate 1200 is used for cuboid fixation with screws 1120 inserted into the calcaneus 1109 and/or talus 1113 with a lateral to medial approach, and screws inserted into the cuboid with a plantar to dorsal approach. The plate 1200 has a cuboid portion 1204 with the same size and shape as the plantar-medial portion 1104 of the plate 1100 described above, but has a lateral portion 1202 which is shorter than the dorsal portion 1102 of the plate 1100. For example, in plate 1100, the dorsal portion 1102 is long enough to include four locking holes 1118 in each row. In plate 1200, the lateral portion 1202 is long enough to include two locking holes 1118 in each row. In other respects, the configuration of the plate 1200 is similar to that of the plate 1110.

Figure 6:
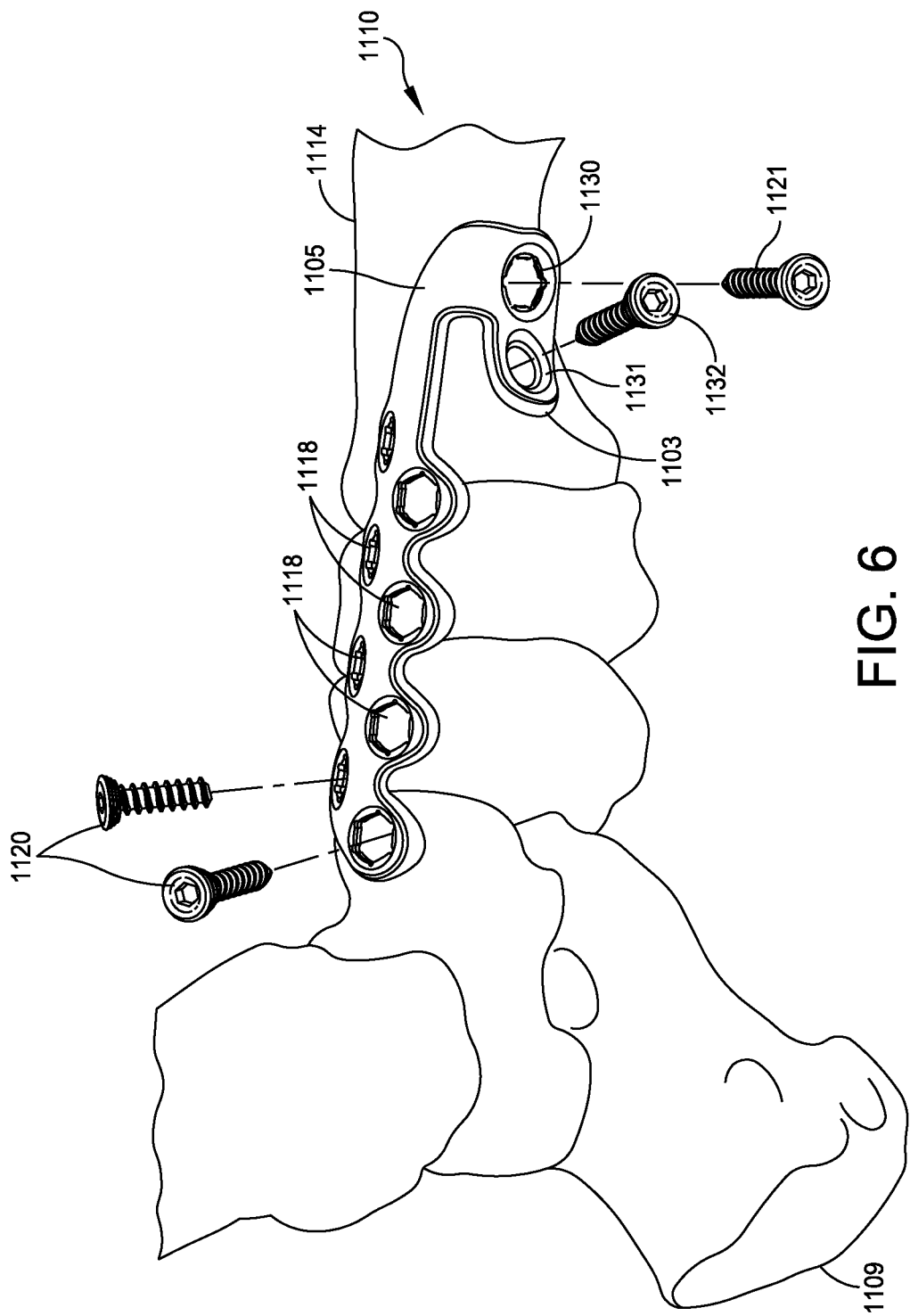
FIG. 6 is a medial view showing the foot and bone plate of FIG. 5, with the bone plate in position on the foot.
Figure 7:
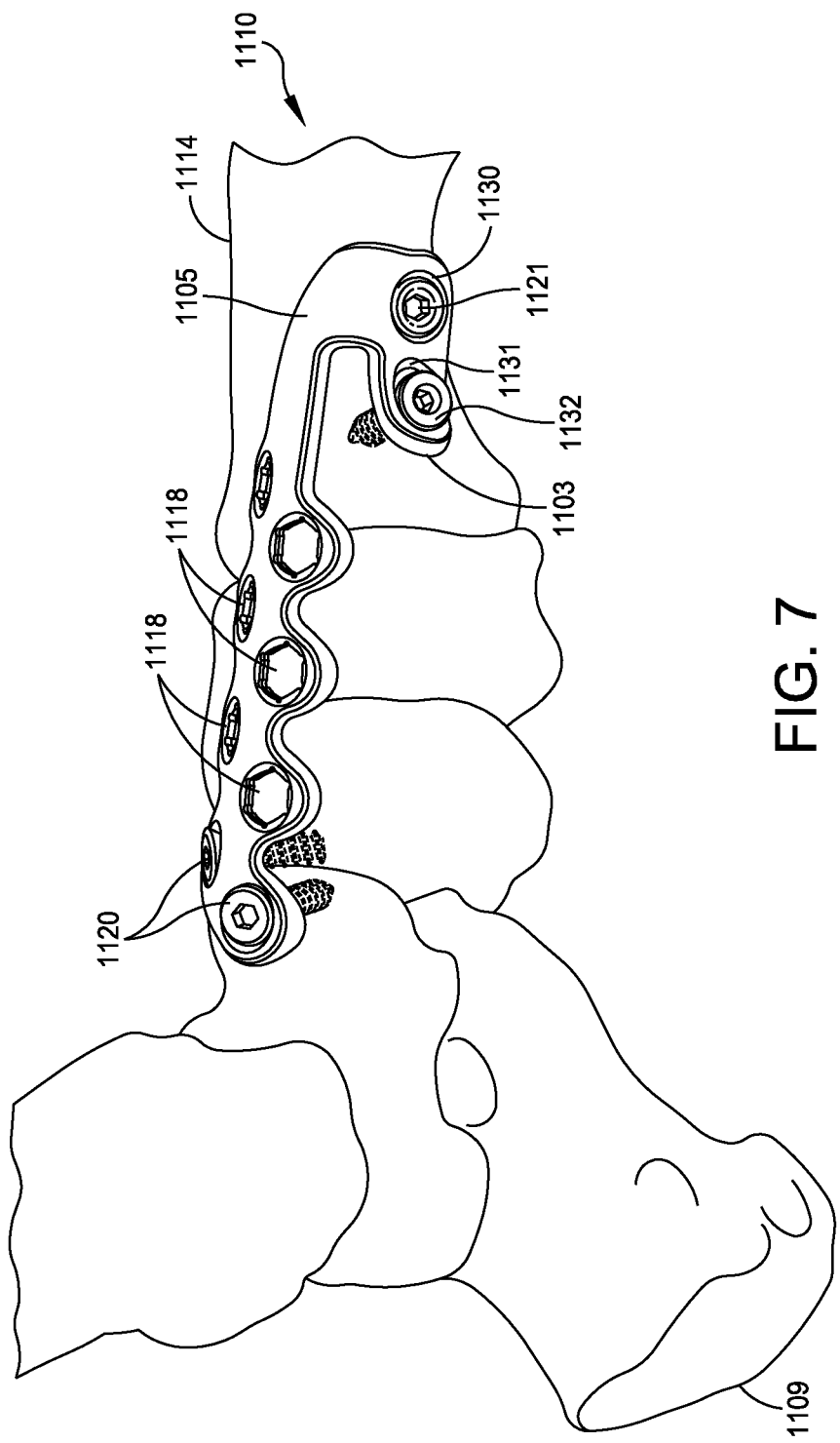
FIG. 7 is a medial view showing the foot with the bone plate in place and screws inserted.

FIGS. 9A-11 show the plate 1200, rotated about 90 degrees from the position of plate 1100 in FIG. 6. The lateral portion 1202 of plate 1200 is mainly positioned on the lateral side of the foot, whereas the corresponding dorsal portion 1102 of the plate 1100 is mainly positioned on the medial side of the foot. The cuboid portion 1204 of plate 1200 is mainly positioned on the plantar-lateral side of the foot, whereas the corresponding plantar-medial portion 1104 of the plate 1100 is mainly positioned on the plantar-medial side of the foot.

The plate 1200 is a unitary plate configured to conform to a foot 1110 of a patient. The unitary plate 1200 has a lateral portion 1202 shaped to conform to a lateral surface calcaneus 1109 of the foot 1110, and a cuboid portion 1204 shaped to conform to a plantar surface of the cuboid 1111 of the foot 1110. The cuboid portion 1204 is integrally attached by the connecting portion 1205 to the lateral portion 1202. The cuboid portion 1204 is shaped to extend to a plantar surface of the cuboid bone. As shown in FIGS. 9A-11, the cuboid portion 1204 wraps around the lateral surface of the cuboid bone 1111 and then extends in a posterior direction along the calcaneus 1109, creating a tension band with bone screws 1120, 1121 extending in approximately orthogonal directions.

The unitary plate 1200 has a plurality of apertures 1118, 1130 for receiving bone screws 1120. The apertures include first apertures 1118 and one or more second apertures 1130. The bone screws 1120 can be locking or non-locking bone screws.

The lateral portion 1202 of the plate 1200 has a plurality of first apertures 1118 therethrough, including one or more apertures adapted to receive a respective one or more first bone screws 1120 to be inserted into a lateral surface of a calcaneus 1109 and/or talus 1113. In some embodiments, the lateral portion 1202 of the plate has a first row of first apertures 1118 and a second row of first apertures 1118. The first row and second row of first apertures 1118 are configured to receive bone screws, which can be locking screws 1120 or non-locking screws. The second row of first apertures 1118 is longitudinally offset from the first row of first apertures 1118, to provide several insertion locations for bone screws. For optimal stability, at least one bone screw is inserted through the first apertures 1118 into the calcaneus 1109 and at least one of the talus or the navicular.

In some embodiments, the lateral portion 1202 of the plate has a radius R on its inner surface (best seen in FIG. 11), which is substantially constant from the posterior end of the plate 1200 to the anterior-most aperture 1118 of the lateral portion 1202. The radius can be the same for various bone plate sizes having different posterior-anterior lengths. For example, in some embodiments, the radius size is 0.53 inch (the same as the radius of the portion 1102 of plate 1100). This radius size conforms comfortably to the lateral surface of the bones 1109, 1113. In various embodiments, the posterior-anterior length and number of holes in the lateral portion 1202 can be varied.

The cuboid portion 1204 of the bone plate 1200 has at least one second aperture 1130 adapted to receive a second bone screw 1121 inserted through a distal (anterior) end of the cuboid portion 1204 into the cuboid bone 1111 of the foot 1110.

In some embodiments, the cuboid portion 1204 further includes a compression slot 1131. The compression slot 1131 is proximate an anterior end of the unitary plate 1200. In some embodiments, as shown in FIGS. 9A-11, the cuboid portion 1204 has both a compression slot 1131 and at least one second aperture 1130. The compression slot 1131 is placed closest to the proximal (posterior) end of the cuboid portion 1204 of the plate 1200. The compression slot 1131 has a ramped edge. The compression slot 1131 is configured to receive a non-locking screw 1132 which can be driven through the compression slot 1131 into the cuboid bone 1111.

In some embodiments, the cuboid portion 1204 comprises an oblique portion extending in a posterior-plantar direction, the oblique portion configured to conform to the calcaneus 1109 of the foot 1110, and the compression slot 1131 is located in the oblique portion. The second aperture 1130 is located in a horizontal portion.

Figure 11:
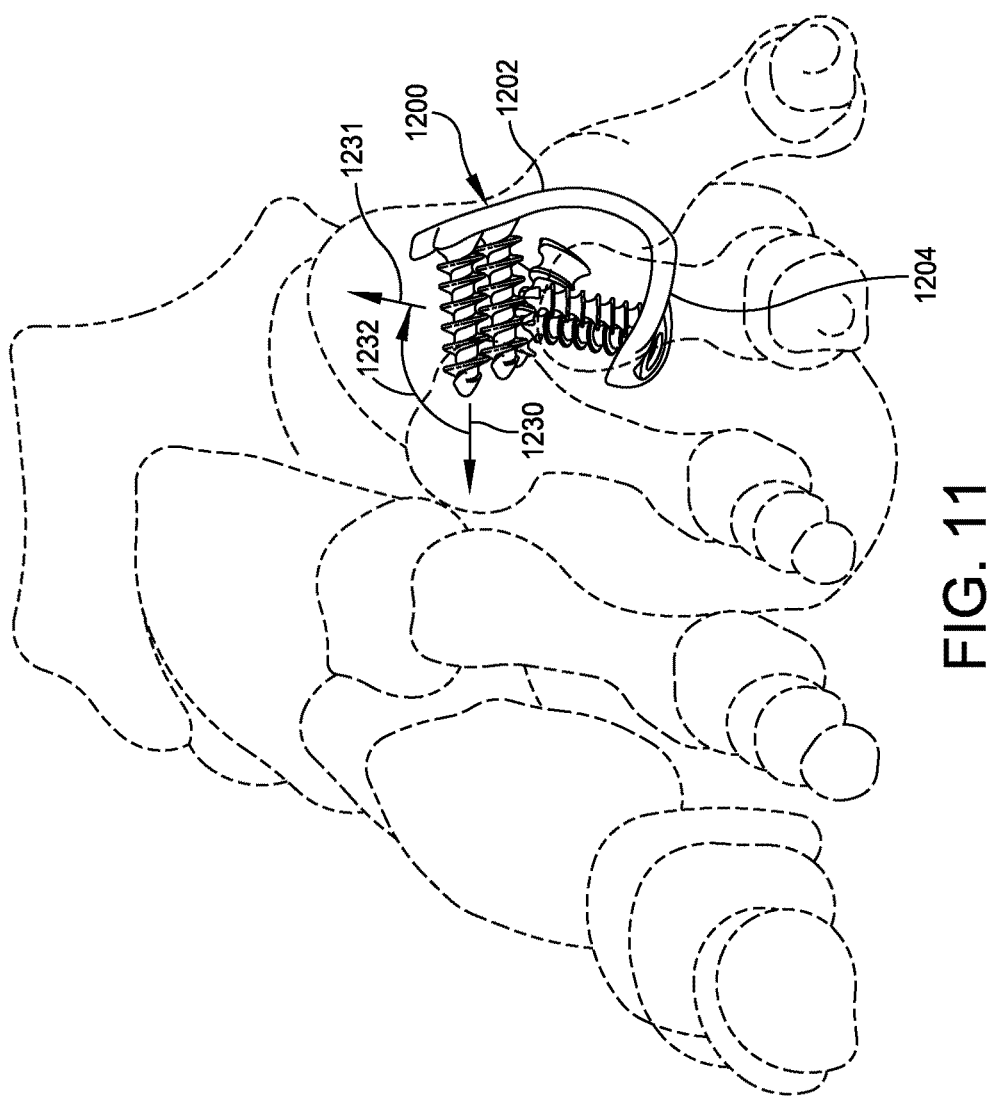
FIG. 11 is an anterior view of the foot and plate of FIG. 9A.

In some embodiments, as best seen in FIG. 11, the first apertures 1118 and second apertures 1130 are oriented relative to each other so that an angle between one of the first bone screws 1120 and the second bone screw 1121 after insertion is in a range from about 60 degrees to about 120 degrees. In some embodiments, a respective angle between the compression screw and each of the one or more bone screws is in a range from about 75 degrees to about 90 degrees.

In some embodiments, as best seen in FIG. 11, the lateral portion 1202 has a first average normal direction 1231 and the plantar portion 1204 has a second average normal direction 1230, and an angle 1232 between the first average normal direction and the second average normal direction is about 95 degrees.

In other respects, such as material selection and fabrication methods, the plate 1200 can be the same as the plate 1100. The procedure using the plate 1200 is similar to that described above with respect to plate 1100, except for the positioning of the plate 1200 and screws, 1120, 1121, 1132.

In some embodiments, after positioning the plate 1200 as show in FIGS. 9A-11, a compression screw 1132 is inserted through the compression slot 1131 in the plantar portion 1204 and into the cuboid bone 1111. In some embodiments, the step of inserting the compression screw 1132 causes compression of the lateral column, to compress the joint until the cuboid and calcaneus start touching each other. The compression slot 1131 has a ramped edge. A non-locking screw 1132 is positioned at the most anterior (distal) end of the compression slot 1131 and driven through the compression slot 1131 into the bone 1109. As the head of the non-locking screw 1132 is driven into the compression slot 1131, the head rides along the anterior ramp of the compression slot and centers itself in the aperture 1131, applying a force on the plate 1200 to pull the posterior end of the plate (and the calcaneus 1109) in the anterior direction. The amount of tension can be determined by the geometry of the compression slot and its ramp. For example, in some embodiments, the compression slot causes 5 mm of compression. That is, the bone screws 1120 inserted through the lateral portion 1202 of the plate 1200 are drawn 5 mm closer to the anterior end of the fifth metatarsal.

After inserting the compression screw 1132, at least one additional bone screw 1121 is inserted through the aperture 1130 in the distal (anterior) end of the plantar portion 1204, till the bone screw is inserted into the cuboid of the foot 1110. The bone screw 1121 can be a locking screw or a non-locking screw. In some embodiments, the bone screw 1121 is a polyaxial screw. In some embodiments, the bone screw is an osteopenic screw. In some embodiments, the bone screw 1121 is inserted from an angle δ of 15 to 20 degrees below the dorsal-plantar axis, so that the insertion angle of bone screw 1121 has a lateral component of about 15 to about 20 degrees.

The surgeon inserts additional bone screws 1120 into the lateral portion 1202 of the plate 1200. In some embodiments, the surgeon inserts a bone screw 1120 into each of the remaining holes 1118 which overlies bone (and does not overlie a joint). In embodiments in which the lateral portion 1202 of the plate has a first row of holes and a longitudinally offset second row of holes, the surgeon can insert one or more locking bone screws 1120 through the first and second rows of holes, into one or more of the talus 1122, navicular 1124 or cuneiform 1126 bones. The screws 1120 are placed within a 30 degree purchase-cone so that bone screws 1120 always purchase the bones of talus 1122, navicular 1124 and/or cuneiform 1126, i.e., always acquire a leveraged and secure engagement between the threads on the surface of bone screw 1120 and the interior of the bone as the screw is rotated inwardly toward the bone.

In some embodiments, the step of inserting the one or more bone screws includes inserting at least one bone screw 1120 in each of the talus 1122, the navicular 1124, and the cuneiform 1126. In some embodiments, the step of inserting the one or more bone screws includes inserting at least two bone screws 1120 in each of the talus 1122, the navicular 1124, and the cuneiform 1126. In some embodiments, two bone screws are inserted into each bone 1122, 1124, 1126, including one bone screw in the first longitudinal row, and one bone screw in the second longitudinal row.

Although an example of a shorter plate 1200 is shown and described for cuboid fixation, a longer plate, similar in length to the plate 1100, or a plate (not shown) having six apertures 1118 on the lateral portion 1202 can be used in the position shown in FIGS. 9A to 11, for fixation of the entire lateral column. For example the plate can be positioned so that the plantar portion is placed against the fifth metatarsal. The surgeon inserts a bone screw 1120 through the posterior-most aperture 1118 into the calcaneus. Insertion of the compression screw 1132 into the fifth metatarsal causes the fifth metatarsal, cuboid and calcaneus to draw together.

Although the examples described above use a relatively long plate 1100 for the dorsal and medial sides of the foot and a relatively short plate 1200 for the lateral and plantar sides of the foot, in other embodiments, shorter plates can be used on the dorsal side of the foot, and longer plates can be used on the medial or lateral side.

Although the drawings show a left-foot version of the plates 1100, 1200, right-foot versions of the plates 1100, 1200 are provided as the mirror image of the plates 1100, 1200 with respect to a vertical plane that is normal to the medial-lateral axis.

The plates 1100 and 1200 described herein provide a larger, more stable structure that is advantageous for advanced midfoot reconstruction. The plates described herein can be used in combination with any of a variety of external and/or internal fixation devices. For example, the plate 1100 can be used in combination with external fixation devices such as, but not limited to a cast or a circular fixator; the plates 1100 and 1200 can be used in combination with internal fixation devices such as, but not limited to a medial column wire or beam. The plates 1100 and 1200 aid in keeping the respective medial and lateral columns fused while also handling large loads applied to the midfoot.

Although the subject matter has been described in terms of exemplary embodiments, it is not limited thereto. Rather, the appended claims should be construed broadly, to include other variants and embodiments, which may be made by those skilled in the art.

What is claimed is:

1. An article, comprising:
   a unitary plate configured to conform to a foot of a patient, the unitary plate having a dorsal portion shaped to conform to a dorsal surface of a medial column of the foot and a plantar-medial portion shaped to conform to a medial surface of a first metatarsal of the foot and extend to a plantar surface of the first metatarsal, the plantar-medial portion integrally attached to the dorsal portion, the unitary plate having a plurality of apertures for receiving screws, the apertures including:
   a plurality of first apertures through the dorsal portion, including one or more apertures adapted to receive a respective one or more first screws to be inserted into a dorsal surface of a talus of the foot, and
   at least one second aperture adapted to receive a second screw inserted through a plantar end of the plantar-medial portion into a first metatarsal of the foot, wherein the dorsal portion of the unitary plate has a first row of first apertures and a second row of first apertures, the first and second rows of first apertures are configured to receive locking screws, and the second row of first apertures is longitudinally offset from the first row of first apertures.

2. The article of claim 1, wherein the plantar portion further includes a compression slot.

3. The article of claim 2, wherein the compression slot is proximate an anterior end of the unitary plate distal from the first apertures.

4. The article of claim 1, wherein the plantar-medial portion comprises an oblique portion extending in a posterior-medial direction, the oblique portion configured to conform to the first metatarsal of the foot, and the second aperture is located in the oblique portion.

5. The article of claim 1, wherein the foot has a navicular and a cuneiform, and the first apertures are arranged to permit inserting the first screws through the first apertures into each of the talus, the navicular, and the cuneiform.

6. The article of claim 1, wherein the dorsal portion has a first average normal direction and the plantar-medial portion has a second average normal direction, and an angle between the first average normal direction and the second average normal direction is about 95 degrees.

7. An article, comprising:
   a unitary plate configured to conform to a foot of a patient, the unitary plate having a lateral portion shaped to conform to a lateral surface of a lateral column of the foot, and a plantar portion shaped to extend to conform to a plantar surface of a cuboid bone of the foot, the plantar portion integrally attached to the lateral portion, the unitary plate having a plurality of apertures for receiving screws, the apertures including:
   a plurality of first apertures through the lateral portion, including one or more apertures adapted to receive a respective one or more first screws to be inserted into a lateral surface of a calcaneus of the foot,
   at least one second aperture adapted to receive a second screw inserted through the plantar portion into a cuboid bone of the foot; and
   wherein the lateral portion of the unitary plate has a first row of first apertures and a second row of first apertures, the first and second rows of first apertures are configured to receive locking screws, and the second row of first apertures is longitudinally offset from the first row of first apertures.

8. The article of claim 7, wherein the plantar portion further includes a compression slot proximate an anterior end of the unitary plate distal from the first apertures.

9. The article of claim 7, wherein the plantar portion comprises an oblique portion extending in a plantar-posterior direction, the oblique portion configured to conform to the cuboid bone of the foot, and the second aperture is located in the oblique portion.

10. The article of claim 7, wherein the lateral portion has a first average normal direction and the plantar portion has a second average normal direction, and an angle between the first average normal direction and the second average normal direction is about 95 degrees.

* * * * *